(12) United States Patent
Siedler et al.

(10) Patent No.: US 10,052,580 B2
(45) Date of Patent: Aug. 21, 2018

(54) TRIM BED FOR ADSORPTION SEPARATION ZONE

(71) Applicant: UOP LLC, Des Plaines, IL (US)

(72) Inventors: Nathan Siedler, Palatine, IL (US); Charles P. Luebke, Mount Prospect, IL (US); Jayant K. Gorawara, Buffalo Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/686,019

(22) Filed: Aug. 24, 2017

(65) Prior Publication Data

US 2018/0178159 A1 Jun. 28, 2018

Related U.S. Application Data

(60) Provisional application No. 62/439,536, filed on Dec. 28, 2016.

(51) Int. Cl.
*C07C 7/13* (2006.01)
*B01D 53/04* (2006.01)

(52) U.S. Cl.
CPC ..... *B01D 53/0423* (2013.01); *B01D 53/0454* (2013.01); *C07C 7/13* (2013.01); *B01D 2253/108* (2013.01); *B01D 2256/24* (2013.01); *B01D 2257/7027* (2013.01); *B01D 2259/402* (2013.01); *B01D 2259/40083* (2013.01)

(58) Field of Classification Search
None
See application file for complete search history.

(56) References Cited

U.S. PATENT DOCUMENTS

| 3,636,679 A * | 1/1972 | Batta ................... B01D 53/047 95/100 |
| 3,824,182 A * | 7/1974 | Peterson ............ B01D 15/1885 208/188 |
| 3,973,931 A * | 8/1976 | Collins ................ B01D 53/047 95/130 |
| 4,026,680 A * | 5/1977 | Collins .............. B01D 53/0423 95/130 |
| 5,220,099 A | 6/1993 | Schreiner et al. |
| 5,223,145 A * | 6/1993 | Markovs ................ B01D 15/00 210/673 |
| 5,338,450 A * | 8/1994 | Maurer .............. B01D 53/0446 210/286 |
| 6,106,702 A | 8/2000 | Sohn et al. |
| 7,576,248 B2 | 8/2009 | Kulprathipanja et al. |
| 3,034,973 A1 | 10/2011 | Goncalvez De Almeida et al. |
| 8,778,050 B2 * | 7/2014 | Dolan ..................... C10L 3/101 95/96 |

(Continued)

OTHER PUBLICATIONS

Search Report dated Jan. 25, 2018 for corresponding PCT Appl. No. PCT/US2017/055864.

*Primary Examiner* — Tam M Nguyen

(57) ABSTRACT

Methods for operating an adsorption separation zone are described. A trim bed is used with two adsorption beds in a swing bed arrangement. The trim bed will catch small amounts of treated feed remaining in the adsorption bed during the switch over from the spent adsorption bed to the fresh adsorption bed. In addition, any adsorbed material that desorbs from the spent adsorption bed during the displacement step of regeneration would be adsorbed onto the trim bed.

20 Claims, 11 Drawing Sheets

(56) References Cited

U.S. PATENT DOCUMENTS

2010/0116711 A1    5/2010  Wong et al.
2012/0160742 A1    6/2012  Sohn et al.
2015/0065765 A1*  3/2015  Villechange ........... C10G 25/00
                                                      585/254

* cited by examiner

TRIM BED FOR ADSORPTION SEPARATION ZONE

CROSS-REFERENCE TO RELATED APPLICATION

This application claims priority from Provisional Application No. 62/439,536 filed Dec. 28, 2016, the contents of which cited application are hereby incorporated by reference in its entirety.

BACKGROUND OF THE INVENTION

Adsorptive separation is applied to the recovery of a variety of hydrocarbon and other chemical products. Chemical separations using this approach include: the separation of mixtures of aromatics into specific aromatic isomers, the separation of linear from nonlinear aliphatic and olefinic hydrocarbons, the separation of either paraffins or aromatics from a feed mixture comprising both aromatics and paraffins, the separation of chiral compounds for use in pharmaceuticals and fine chemicals, the separation of oxygenates such as alcohols and ethers, and the separation of carbohydrates such as sugars.

Packed beds of adsorbent materials are typically used in adsorption processes. Adsorbent materials are generally in the form of spherical beads, or pellets. Adsorbent materials are typically oxygen-containing compounds, carbon-containing compounds, or polymer-based compounds. Oxygen-containing compounds can be, for example, hydrophilic and polar, including materials such as silica gel and zeolites. Carbon-based compounds can be, for example, hydrophobic and non-polar, including materials such as activated carbon and graphite. Polymer-based compounds can be, for example, polar or non-polar functional groups in a porous polymer matrix.

In operation, a process stream is introduced into an adsorption bed, and the adsorbent material contained therein removes a desired or undesired component from the stream as it filters through the adsorption bed. After a given time period, the adsorbent material becomes saturated with the sorbate, and the adsorption process in that adsorption bed must be stopped in order to regenerate the adsorbent and remove the sorbate. After a regeneration cycle is complete, a new adsorption cycle can begin. Adsorption processes often operate in a swing bed arrangement so that one or more beds are active, and one or more beds are being regenerated.

Several problems can occur during operation with a swing bed arrangement. First, feed can be lost when switching a bed from active state to regeneration. In addition, there is a risk that when the adsorption bed is full, some of the material which is supposed to be adsorbed in the adsorption bed will flow through the adsorption bed and not be captured.

Thus, there exists a need for an improved method for operating an adsorption separation zone.

SUMMARY OF THE INVENTION

One aspect of the invention is a method for operating an adsorption separation zone. In one embodiment, the adsorption separation zone includes at least two adsorption beds and a trim bed. The adsorption beds and the trim beds are in selective communication so that they can be connected and disconnected as needed during the process. Untreated feed is passed through the first adsorption bed to produce treated feed, and the treated feed is passed out through a product outlet. At the same time, fresh desorbent is passed through the second adsorption bed and the trim bed to remove adsorbed material, regenerating the second adsorption bed and the trim bed. Spent desorbent is formed which passes out though a desorbent outlet. When the adsorbed material is desorbed from the second adsorption bed and the trim bed, the flow of fresh desorbent to the second adsorption bed and the trim bed is stopped, and the second adsorption bed and the trim bed are isolated from the first desorbent inlet and the desorbent outlet. At the same time, the untreated feed continues to pass through the first adsorption bed and the treated feed continues to pass out through the product outlet. When the first adsorption bed is spent, the flow of the untreated feed to the first adsorption bed is stopped. The untreated feed is then passed through the second (fresh) adsorption bed to produce additional treated feed. The additional treated feed displaces the desorbent in the second adsorption bed. The desorbent from the second adsorption bed passes to the first adsorption bed where the desorbent displaces the treated feed. The treated feed from the first adsorption bed passes to the trim bed where it displaces the desorbent in the trim bed. The desorbent from the trim bed and the treated feed from the first adsorption bed pass out through the product outlet. When substantially all of the desorbent is displaced from the second adsorption bed, the first adsorption bed and the trim bed are isolated from the second adsorption bed and the product outlet. The treated feed from the first adsorption bed and the trim bed is passed to the second adsorption bed. The untreated feed continues to pass through the second adsorption bed, and the additional treated feed continues to pass out through the product outlet. A second desorbent is then passed through the first adsorption bed and the trim bed to remove any residual treated feed from the first adsorption bed. The treated feed from the first adsorption bed and the trim bed continues to pass to the second adsorption bed. The untreated feed continues to pass through the second adsorption bed, and the additional treated feed continues to pass out through the product outlet. When the residual treated feed is removed from the first adsorption bed, the first adsorption bed is isolated from the second desorbent inlet. The second desorbent is passed through the trim bed to remove the treated feed from the trim bed. The treated feed from the first adsorption bed and the trim bed continues to pass through the second adsorption bed, and the untreated feed continues to pass through the second adsorption bed and the additional treated feed continues to pass out through the product outlet. When the trim bed is full of the second desorbent, the flow of the second desorbent is stopped. The trim bed is isolated from the second adsorption bed, while the untreated feed continues to pass through the second adsorption bed and the additional treated feed out continues to pass through the product outlet. Fresh desorbent is then passed through the first adsorption bed and the trim bed to remove adsorbed material to regenerate them. Additional spent desorbent is formed which passes out through the desorbent outlet. The untreated feed continues to pass through the second adsorption bed, and the additional treated feed continues to pass out through the product outlet.

DETAILED DESCRIPTION OF THE INVENTION

Figure 1:
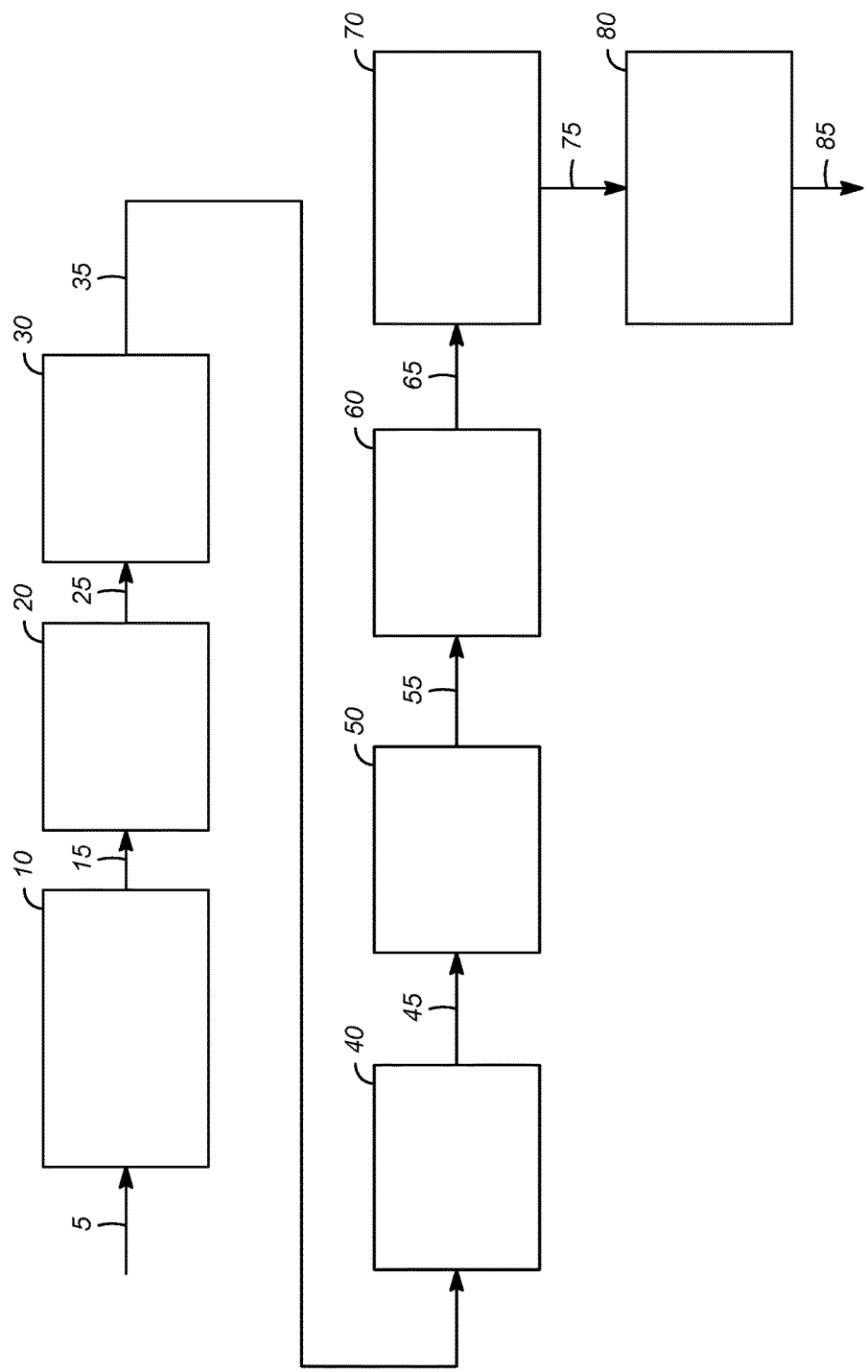
FIG. 1 is an illustration of one embodiment of an integrated process of making linear alkylbenzene (LAB) from a kerosene feed.

This invention helps to mitigate the risk for both heavy aromatics breakthrough and feed losses, regardless of whether the regeneration is countercurrent or co-current when used with a two adsorption bed swing arrangement. In addition to the two adsorption beds, a trim bed is added. The addition of the trim bed will catch the small amounts of heavy aromatics remaining in the adsorption bed during the switch over from the spent adsorption bed to the fresh adsorption bed. In addition, any adsorbed material, e.g., heavy aromatics in an aromatics removal zone, that desorbs from the spent adsorption bed during the displacement step of regeneration would be adsorbed onto the fresh adsorption bed. The trim bed is regenerated with the spent adsorber.

The regeneration steps are set up to minimize feed losses and heavy aromatics breakthrough. The process can be controlled by sampling the effluent from the trim bed or using on-line analyzers, for example. The flow to the trim bed can be adjusted to maximize recovery of the treated feed. The trim bed is sized based on the amount of heavy aromatics expected to desorb during the displacement step. This is expected to be a minor portion of the total adsorbent volume.

When regeneration of an adsorption bed is triggered, the untreated feed will switch from the spent adsorption bed to the fresh adsorption bed. The flow path is altered so that the desorbent displaced from the fresh adsorption bed is sent to the spent adsorption bed. Treated feed displaced from the spent adsorption bed is sent through the trim bed before being sent on to a subsequent process. The trim bed will re-adsorb any adsorbed material, desorbed during the displacement, such as heavy aromatics in an aromatics removal zone. After substantially all of the desorbent has been displaced from the fresh adsorption bed and the volume has been filled with feed, the flow path is changed so that treated feed from the fresh adsorption bed is sent directly to the subsequent process. By "substantially all," we mean at least about 90 vol %, or at least about 93 vol %, or at least about 95 vol %, or at least about 97 vol %, or at least about 98 vol %. Any leftover desorbent can be sent to the subsequent process. Alternatively, it can be separated from the treated feed. Desorbent from the trim bed will be used to flush any feed remaining in the spent desorbtion bed. When the material exiting the spent adsorption bed is predominantly desorbent, the spent adsorption bed will be isolated, and desorbent will be sent directly to the trim bed. By "predominantly," we mean at least about 95 vol %, or at least about 97 vol %, or at least about 98 vol %, or at least about 99 vol %, or at least about 99.5 vol %. The volume of the trim bed and the associated piping will be displaced into the fresh adsorption bed. This minimizes any feed losses while re-adsorbing any heavy aromatics that desorb during the displacement. After the volume of the trim bed has been displaced into the fresh adsorption bed, the spent adsorption bed and the trim bed will be regenerated with fresh desorbent.

In one embodiment, the adsorption separation zone comprises at least two adsorption beds and a trim bed in selective communication. An untreated feed is passed through the first adsorption bed to produce treated feed. The treated feed passes out through a product outlet. Fresh desorbent is passed through the second adsorption bed and the trim bed to remove adsorbed material from the second adsorption bed and the trim bed to regenerate the second adsorption bed and the trim bed forming spent desorbent. The spent desorbent passes out through a desorbent outlet. The first adsorption bed is in downstream communication with a feed inlet, the product outlet is in downstream communication with the first adsorption bed, the second adsorption bed is in downstream communication with a first desorbent inlet, the trim bed is in downstream communication with the second adsorption bed, and the desorbent outlet is in downstream communication with the trim bed.

When the adsorbed material is desorbed from the second adsorption bed and the trim bed, the flow of fresh desorbent to the second adsorption bed and the trim bed is stopped, and the second adsorption bed and the trim bed are isolated. The untreated feed continues to pass through the first adsorption bed, and the treated feed continues to pass out through the product outlet.

The flow of the untreated feed to the first adsorption bed is then stopped, and the untreated feed is passed through the second adsorption bed to produce additional treated feed. The second adsorption bed is in downstream communication with the feed inlet, the first adsorption bed is in downstream communication with the second adsorption bed, the trim bed is in downstream communication with the first adsorption bed, and the product outlet is in downstream communication with the trim bed. The additional treated feed displaces the desorbent in the second adsorption bed, and the desorbent from the second adsorption bed passes to the first adsorption bed where the desorbent from the second adsorption bed displaces the treated feed in the first adsorption bed. The treated feed from the first adsorption bed passes to the trim bed where the treated feed from the first adsorption bed displaces the desorbent in the trim bed. The desorbent from the trim bed and the treated feed from the first adsorption bed pass out through the product outlet.

When substantially all of the desorbent is displaced from the second adsorption bed, the first adsorption bed and the trim bed are isolated from the second adsorption bed. The untreated feed continues to pass through the second adsorption bed, and the additional treated feed continues to pass out through the product outlet. The second adsorption bed is in downstream communication with the feed inlet, and the product outlet is in downstream communication with the second adsorption bed.

A second desorbent is passed through the first adsorption bed and the trim bed to remove any residual treated feed from the first adsorption bed. The untreated feed continues to pass through the second adsorption bed, and the additional treated feed continues to pass out through the product outlet. The first adsorption bed is in downstream communication with a second desorbent inlet, the trim bed is in downstream communication with the first adsorption bed, and the second adsorption bed is in downstream communication with the trim bed.

When the residual treated feed is removed from the first adsorption bed, the first adsorption bed is isolated from the second desorbent inlet. The second desorbent is passed through the trim bed to remove the treated feed from the trim bed, and the treated feed is passed through the second adsorption bed. The untreated feed continues to pass through the second adsorption bed, and the additional treated feed continues to pass out through the product outlet. The trim bed is in downstream communication with the second desorbent inlet, the trim bed is in downstream communication with the first adsorption bed, and the second adsorption bed is in downstream communication with the trim bed.

When the trim bed is full of the second desorbent, the flow of the second desorbent is stopped, and the trim bed is isolated from the second adsorption bed. The untreated feed continues to pass through the second adsorption bed, and the additional treated feed continues to pass out through the product outlet. The trim bed is in downstream communication with the first adsorption bed.

The fresh desorbent is passed through the first adsorption bed and the trim bed to remove adsorbed material from the first adsorption bed and the trim bed to regenerate the first adsorption bed and the trim bed forming additional spent desorbent. The additional spent desorbent passes out through the desorbent outlet, while the untreated feed continues to pass through the second adsorption bed, and the additional treated feed continues to pass out through the product outlet. The first adsorption bed is in downstream communication with the first desorbent inlet, the trim bed is in downstream communication with the first adsorption bed, and the desorbent outlet is in downstream communication with the trim bed.

The fresh desorbent can be bypassed around the second adsorption bed and the trim bed after stopping the flow of the fresh desorbent to the second adsorption bed and the trim bed.

The first desorbent inlet can be isolated from the desorbent outlet while passing the fresh desorbent through the first adsorption bed and the trim bed.

The first and second desorbents can be the same or different.

The process can be run using a counterflow regeneration process in which the feed flows through the adsorption beds and the trim bed in a downflow arrangement and the regeneration takes place in an upflow arrangement. However, those of skill in the art will understand that it can be used in other process arrangements. For example, it could be used in an all downflow arrangement in which both the feed and the desorbent are in a down flow arrangement in all beds. Alternatively, it could be used in an all upflow arrangement in which the feed and the desorbent are in an upflow arrangement in all beds. In another embodiment, it could be operated so that the feed flows through the adsorption beds and the trim bed in an upflow arrangement and the regeneration takes place in a downflow arrangement. In addition, other flow arrangements are possible, such as one in which the trim bed is operated differently from the adsorption beds.

The method can be used in any type of adsorption separation zone, including, but not limited to, an aromatics removal zone, oxygenates removal zone, nitrile removal zone, and the like.

In a preferred process, the untreated feed comprises mono-olefins, aromatics, and paraffins, the first and second desorbent are benzene, the treated feed comprises mono-olefins and unreacted paraffins, and the first and second adsorption beds comprise a Na faujasite X zeolite adsorbent.

The process will be described in more detail with respect to an aromatics removal zone in a process for making linear alkylbenzene. However, one of skill in the art will recognize that the same process could be used in other adsorption processes.

FIG. 1 illustrates one embodiment of an integrated process for producing linear alkylbenzene from a kerosene feed. The kerosene stream 5 is sent to a prefractionation zone 10 where it is separated into a fraction 15 comprising hydrocarbons having between 10 and 13 carbon atoms. The fraction 15 is sent to a hydrotreating zone 20 for hydrotreating. The hydrotreated stream 25 is sent to an adsorptive separation zone 30 where it is separated into an n-paraffin rich stream 35 and an iso-paraffin rich stream (not shown). The n-paraffin rich stream 35 is sent to a dehydrogenation zone 40 to form olefins. The dehydrogenation effluent 45 contains n-paraffins, mono-olefins, di-olefins, and aromatics. The dehydrogenation effluent 45 is sent to a selective hydrogenation zone 50 where the di-olefins are selectively hydrogenated to mono-olefins. A portion of the selectively hydrogenated effluent 55 is sent to an aromatics removal zone 60 where the aromatics are removed. The effluent 65 from the aromatics removal zone 60, which contains n-paraffins and mono-olefins, is sent to an alkylation zone 70 where benzene is alkylated with the mono-olefins to form alkylbenzene. The effluent 75 from the alkylation zone 70, which contains alkylbenzene, benzene, and n-paraffins, is sent to an alkylbenzene separation zone where the linear alkylbenzene product 85 is recovered.

The operation of the adsorption beds in the aromatics removal zone will be discussed in more detail.

Figure 2:
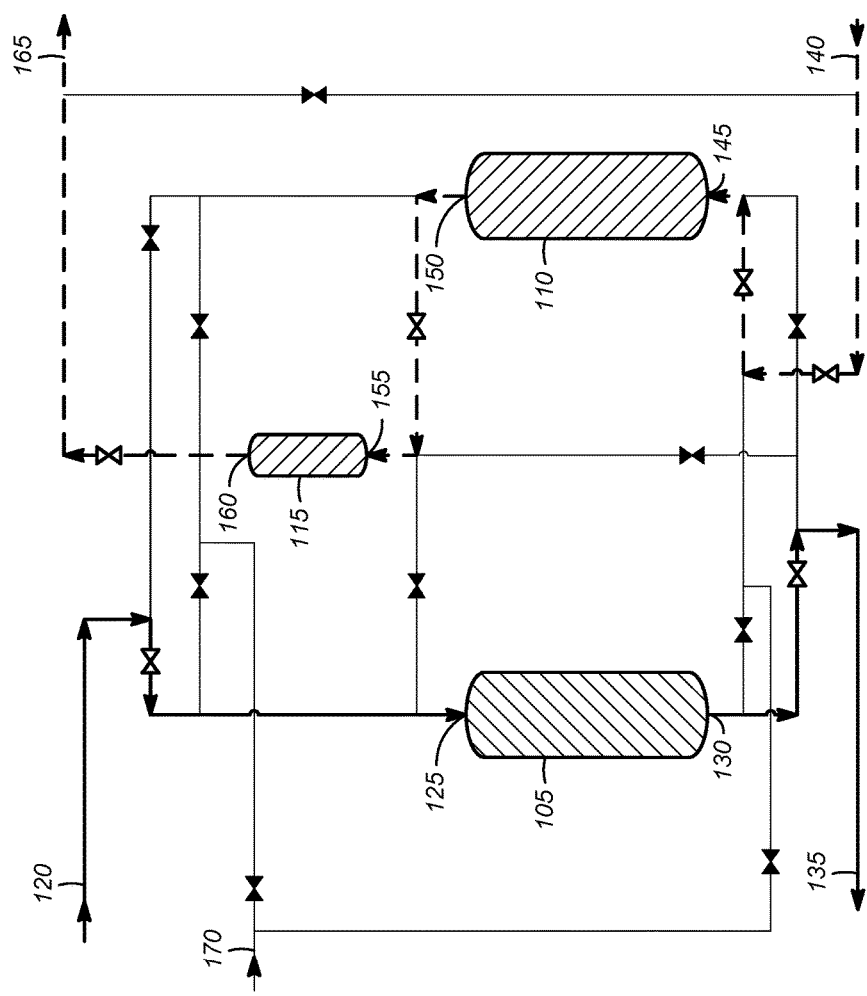
FIGS. 2-11 are an illustration of one embodiment of a method of operating an adsorption separation zone according to the present invention.

In FIG. 2, the first adsorption bed 105 is on-line, and the second adsorption bed 110 and the trim bed 115 are being regenerated. The first adsorption bed 105 is in downstream communication with a feed inlet 120, and a product outlet 135 is in downstream communication with the first adsorption bed 105. As illustrated, the feed inlet 120 is connected to the top 125 of the first adsorption bed 105. The bottom 130 of the first adsorption bed 105 is connected to the product outlet 135. Untreated feed is passed to the top 125 of the first adsorption bed 105 to remove one or more compounds from the feed to produce treated feed. For example, in a linear alkylbenzene (LAB) process, the portion of the effluent from the selective hydrogenation process contains aromatics which need to be removed. The treated feed exits from the bottom 130 of the first adsorption bed 105 and passes out through the product outlet 135.

The first adsorption bed 105 is isolated from the second adsorption bed 110 and the trim bed 115.

The second adsorption bed 110 is in downstream communication with the first desorbent inlet 140, the trim bed 115 is downstream communication with the second adsorption bed 110, and the desorbent outlet 165 is in downstream communication with the trim bed 115. As illustrated, the first desorbent inlet 140 is connected to the bottom 145 of the second adsorption bed 110. The top 150 of the second adsorption bed 110 is connected to the bottom 155 of the trim bed 115. The top 160 of the trim bed 115 is connected with the desorbent outlet 165. Fresh desorbent is passed from the first desorbent inlet 140 to the bottom 145 of the second adsorption bed 110, and from the top 150 of the second adsorption bed 110 to the bottom 155 of the trim bed 115 to remove adsorbed material from the second adsorption bed 110 and the trim bed 115. Removing the adsorbed material regenerates the second adsorption bed 110 and the trim bed 115. The spent desorbent formed during the regeneration the second adsorption bed 110 and the trim bed 115 is passed from the top 160 of the trim bed 115 out through the desorbent outlet 165.

Figure 3:
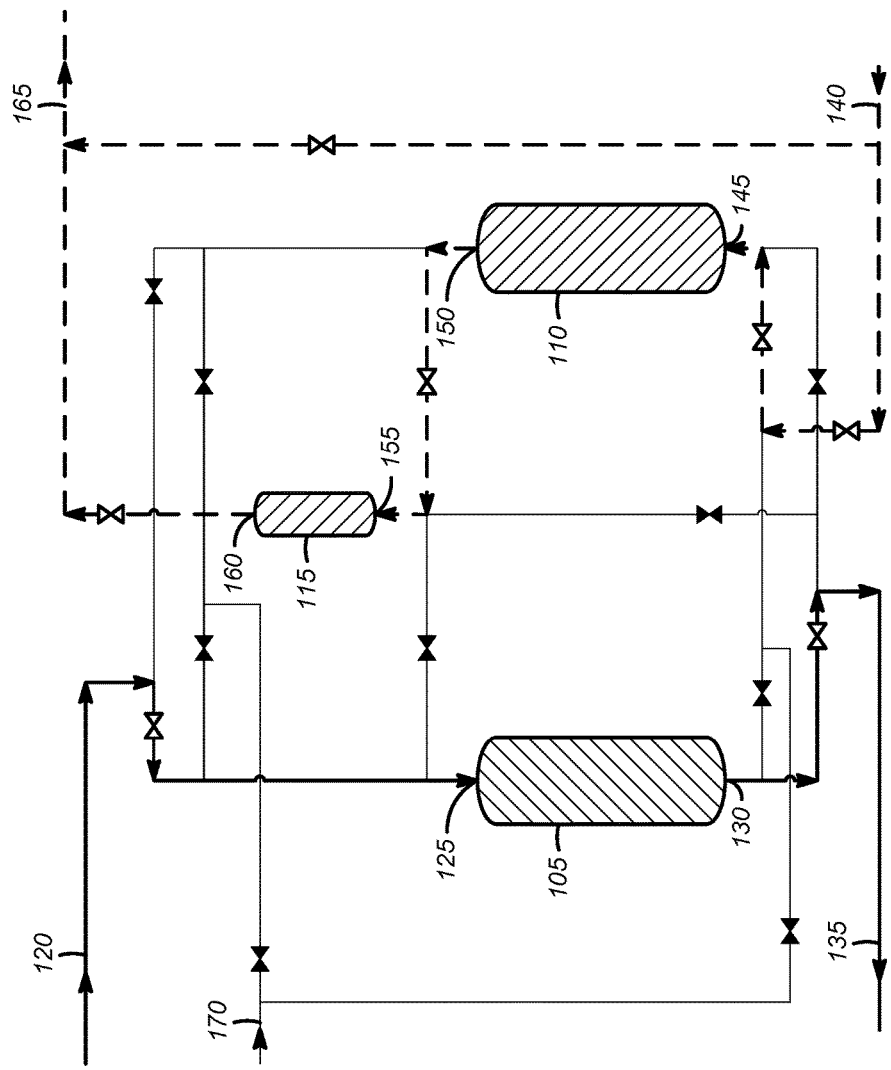

Before or during the desorption process or when it is completed, a connection can be made between the first desorbent inlet 140 and the desorbent outlet 165 so that the desorbent outlet 165 is in downstream communication with the first desorbent inlet 140, as shown in FIG. 3.

Figure 4:
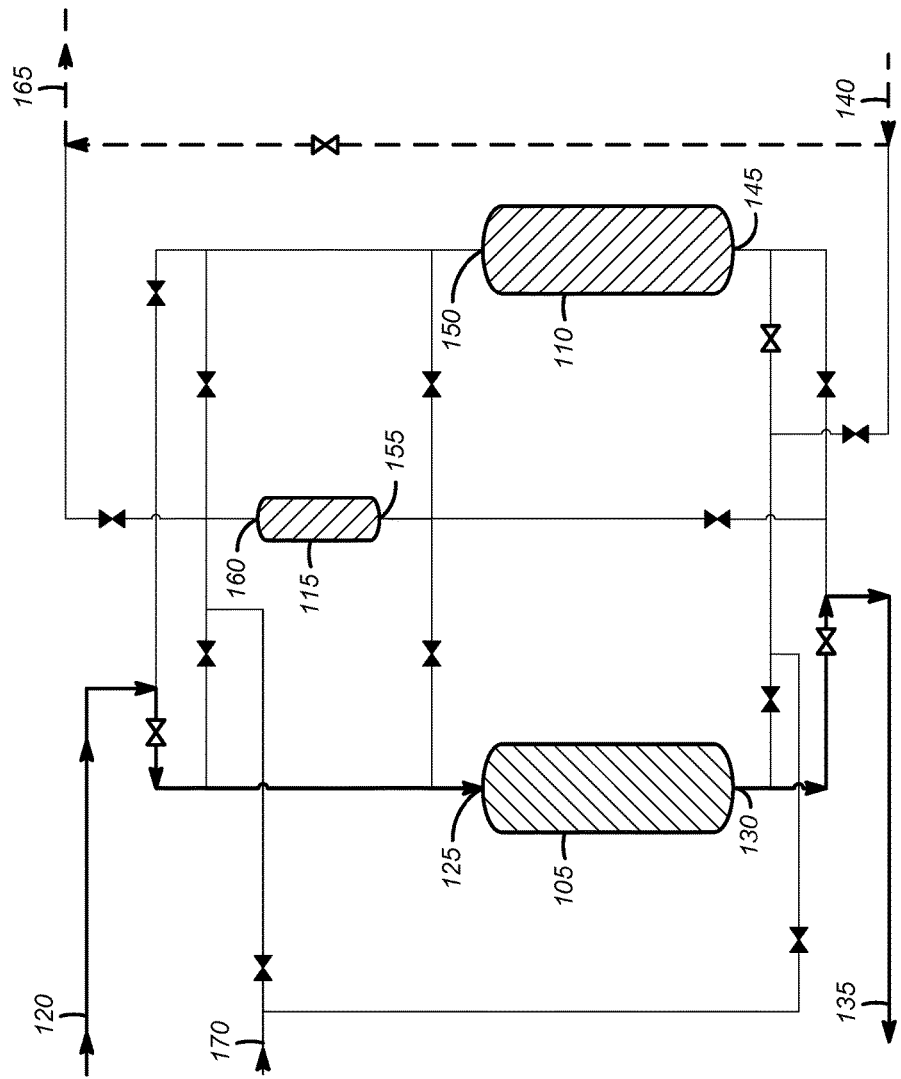

When the adsorbed material is desorbed from the second adsorption bed 110 and the trim bed 115, the flow of fresh desorbent to the second adsorption bed 110 and the trim bed 115 is stopped, as shown in FIG. 4. The second adsorption bed 110 and the trim bed 115 are isolated from the first desorbent inlet 140 and the desorbent outlet 165, and they remain isolated from the first adsorption bed 105. The fresh desorbent bypasses the second adsorption bed 110 and the trim bed 115 and flows from the first desorbent inlet 140 to the desorbent outlet 165. The untreated feed stream continues to pass from the feed inlet 120 through the first adsorption bed 105, and the treated feed passes out through the product outlet 135.

Figure 5:
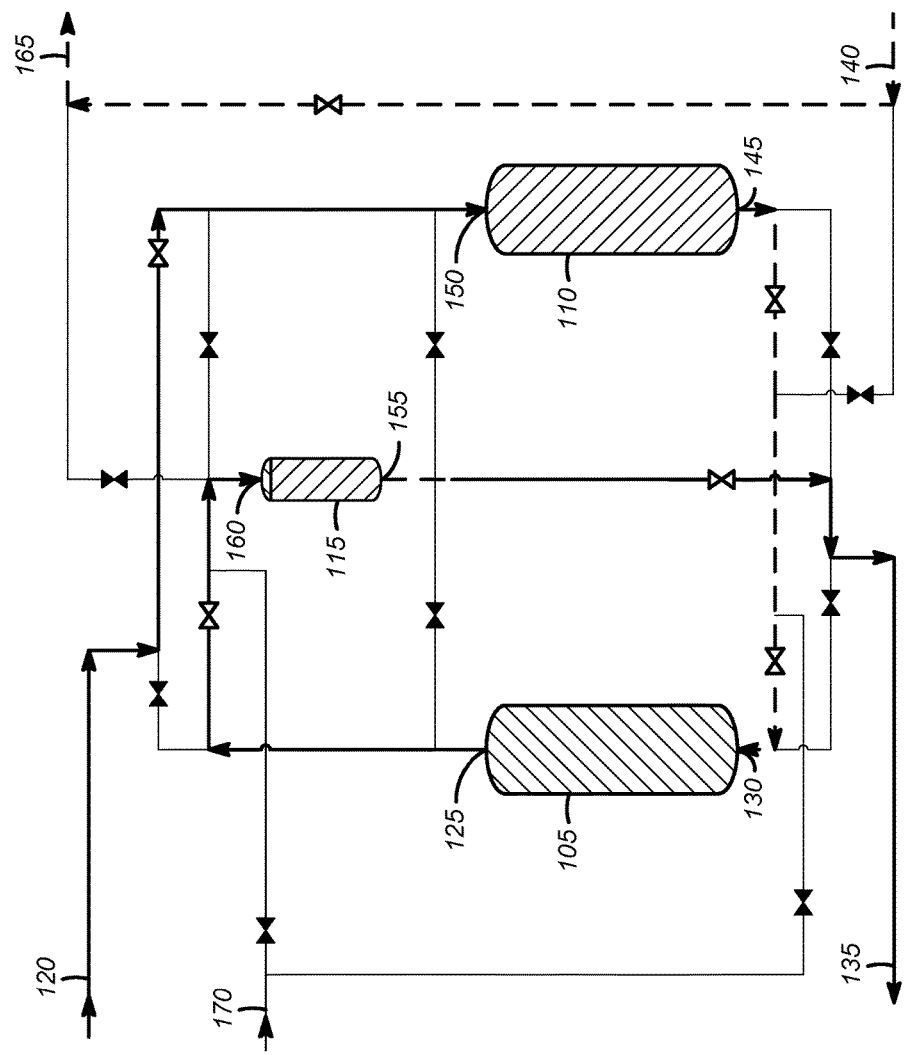

When the first adsorption bed is full of adsorbed material (i.e., spent), the flow of untreated feed to the first adsorption bed 105 is stopped, and the untreated feed passes through the second adsorption bed 110 to produce additional treated feed, as shown in FIG. 5. The second adsorption bed 110 is now in downstream communication with the feed inlet 120. The first adsorption bed 105 is in downstream communication with the second adsorption bed 110. The trim bed 115 is in downstream communication with the first adsorption bed 105, and the product outlet 135 is in downstream communication with the trim bed 115. As illustrated, the feed inlet 120 is connected to the top 150 of the second adsorption bed 110, the bottom 145 of the second adsorption bed 110 is connected to the bottom 130 of the first adsorption bed 125, the top 125 of the first adsorption bed is connected to the top 160 of the trim bed 115, and the bottom 155 of the trim bed 115 is connected to the product outlet 135.

The additional treated feed produced in the second adsorption bed 110 displaces the desorbent in the second adsorption bed 110. The desorbent from the second adsorption bed 110 passes to the first adsorption bed 105 where the desorbent from the second adsorption bed 110 displaces the treated feed in the first adsorption bed 105. The treated feed from the first adsorption bed 105 then passes to the trim bed 115, where the treated feed from the first adsorption bed 105 displaces the desorbent in the trim bed 115. The desorbent from the trim bed 115 and the treated feed from the first adsorption bed 105 pass out through the product outlet 135.

Figure 6:
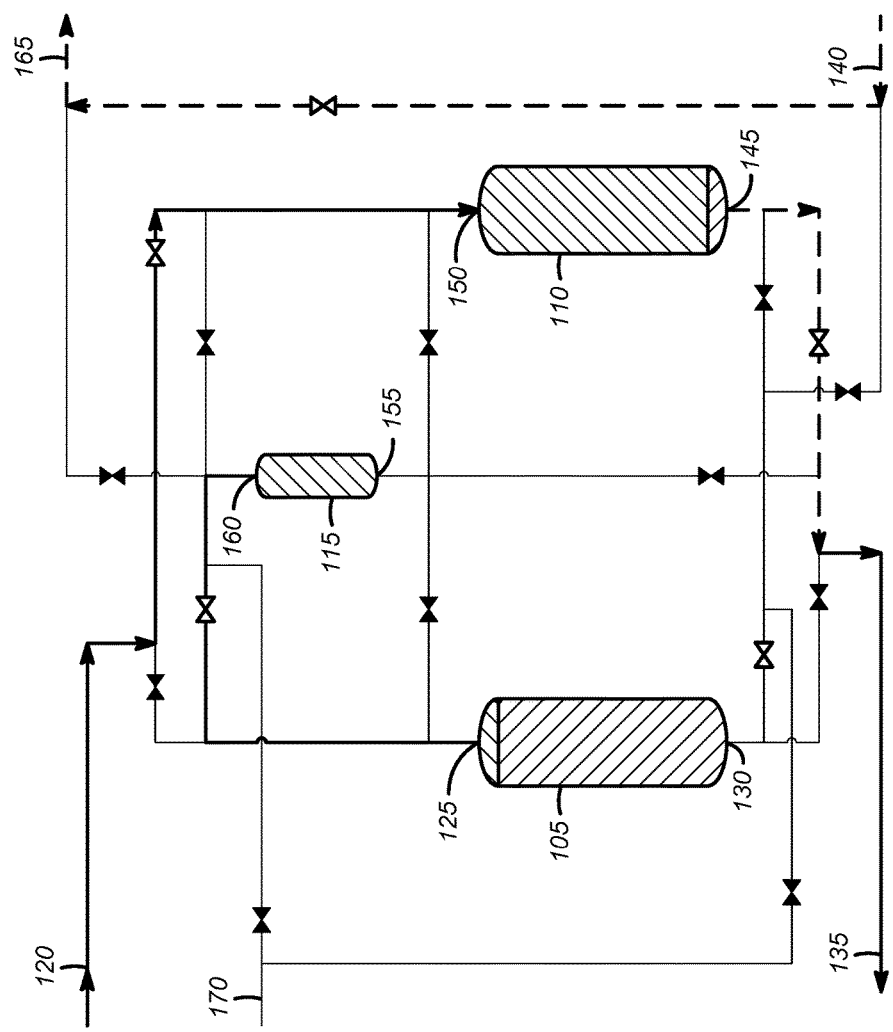

When substantially all of the desorbent is displaced from the second adsorption bed 110, the first adsorption bed 105 and the trim bed 115 are isolated from the second adsorption bed 110, as shown in FIG. 6. The second adsorption bed 110 is in downstream communication with the feed inlet 120, and the product outlet 135 is in downstream communication with the second adsorption bed 110. The trim bed 115 is in downstream communication with the first adsorption bed 105. As illustrated, the bottom 145 of the second adsorption bed 110 is disconnected from the bottom 130 of the first adsorption bed 105, and the bottom of the trim bed 115 is disconnected from the product outlet 135. The bottom 145 of the second adsorption bed 110 is connected to the product outlet 135. As a result, the feed inlet 120 is connected to the top 150 of the second adsorption bed 110, and the bottom 145 of the second adsorption bed 110 is connected to the product outlet 135. The top 125 of the first adsorption bed 105 remains connected to the top 160 of the trim bed 115, and the bottom 130 of the first adsorption bed 105 and the bottom 155 of the trim bed 115 are not connected to anything else. The untreated feed continues to be passed to the top 150 of the second adsorption bed 110 to produce the additional treated feed which is passed out through the product outlet 135.

Figure 7:
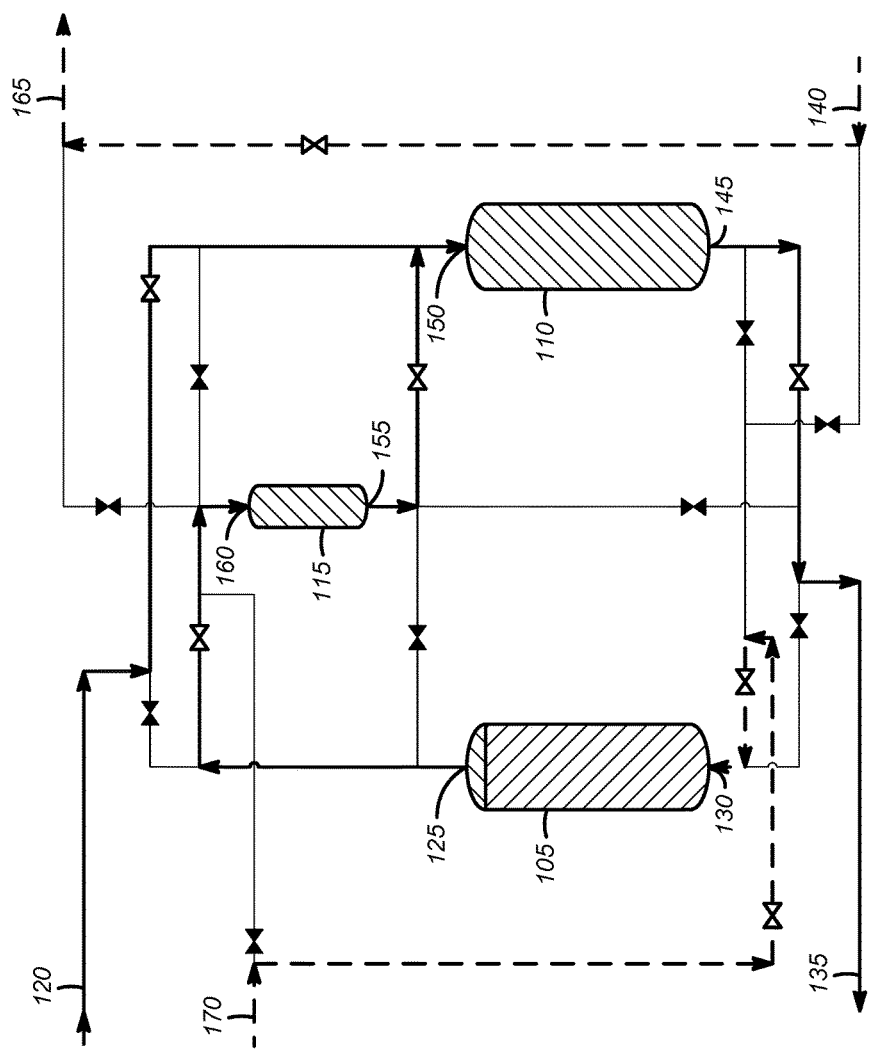

While continuing to pass the untreated feed through the second adsorption bed 110 and the additional treated feed out through the product outlet 135, a second desorbent is passed through the first adsorption bed 105 and the trim bed 115 to remove any residual treated feed from the first adsorption bed 105, as shown in FIG. 7. The second desorbent is passed to the first adsorption bed 105 until the residual treated feed is displaced from the first adsorption bed 105. The first adsorption bed 105 is in downstream communication with a second fresh desorbent inlet 170, the trim bed 115 is in downstream communication with the first adsorption bed 105, and the second adsorption bed 110 is in downstream communication with the trim bed 115. As illustrated, the second desorbent inlet 170 is connected to the bottom 130 of the first adsorption bed 105, the top 125 of the first adsorption bed 105 is connected to the top 160 of the trim bed 115, and the bottom 155 of the trim bed 115 is connected to the top 150 of the second adsorption bed 110.

Figure 8:
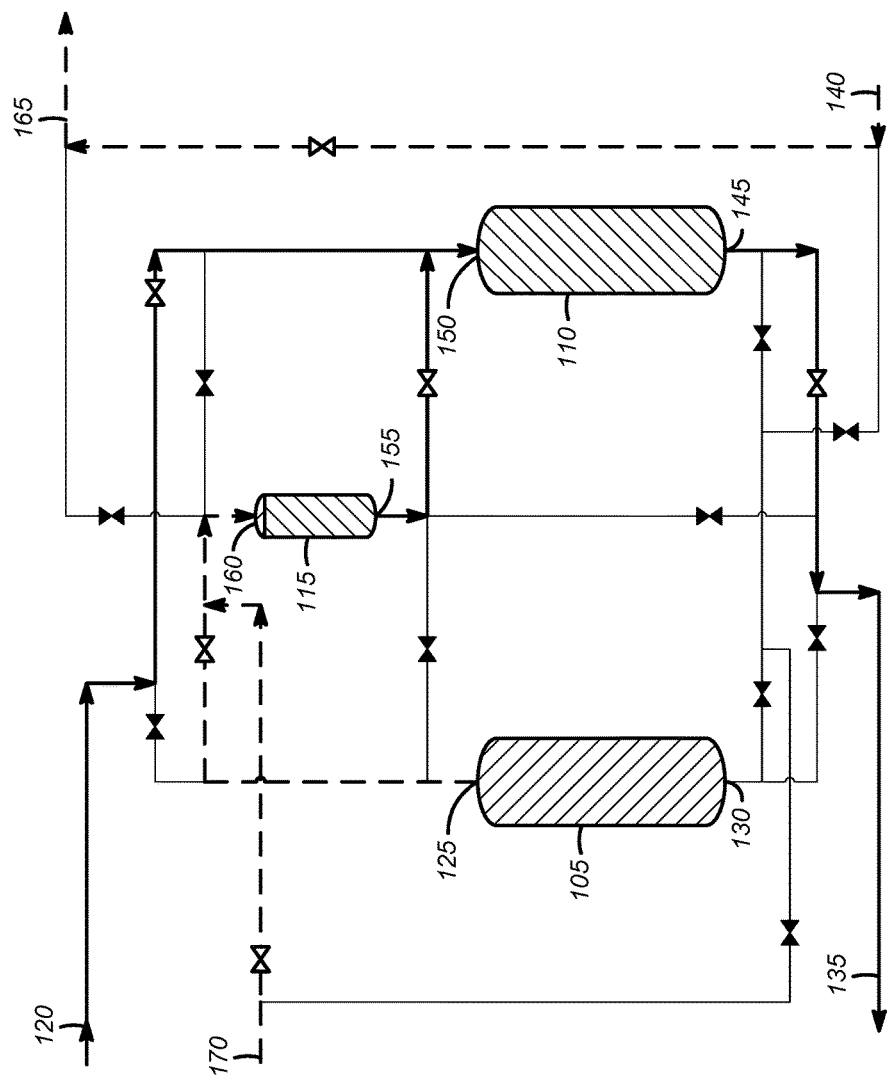

When the residual treated feed is removed from the first adsorption bed 105, the first adsorption bed 105 is isolated from the second desorbent inlet 170, as shown in FIG. 8. The second desorbent is passed from the second desorbent inlet 170 through the trim bed 115 to remove the treated feed from the trim bed 115. The treated feed is passed through the second adsorption bed 110, while continuing to pass the untreated feed through the second adsorption bed 110 to form additional treated feed. The treated feed from the trim bed 115 and the additional treated feed are passed out through the product outlet 135. The trim bed 115 is in downstream communication with the second desorbent inlet 170, and the second adsorption bed 110 is in downstream communication with the trim bed 115. As illustrated, the second desorbent inlet 170 is disconnected from the bottom 130 of the first adsorption bed 105 and connected to the top 160 of the trim bed 115. The bottom 155 of the trim bed 115 remains connected to the top 150 of the second adsorption bed 110.

Figure 9:
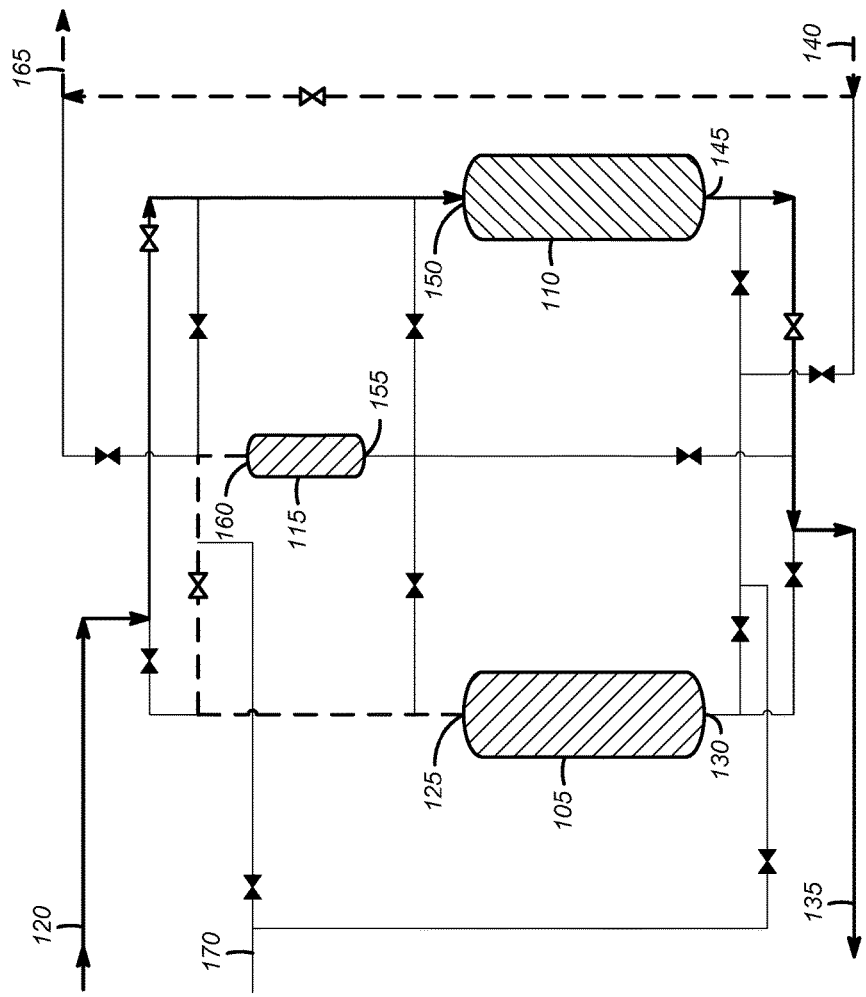

When the trim bed is full of the second desorbent, the flow of the second desorbent is stopped, and the trim bed 115 is isolated from the second adsorption bed 110, as shown in FIG. 9. The untreated feed continues to pass through the second adsorption bed 110, and the additional treated feed continues to pass out through the product outlet 135. As illustrated, the second desorbent inlet 170 is disconnected from the top 160 of the trim bed 115, and the bottom 155 of the trim bed 115 is disconnected from the top 150 of the second adsorption bed 110.

Figure 10:
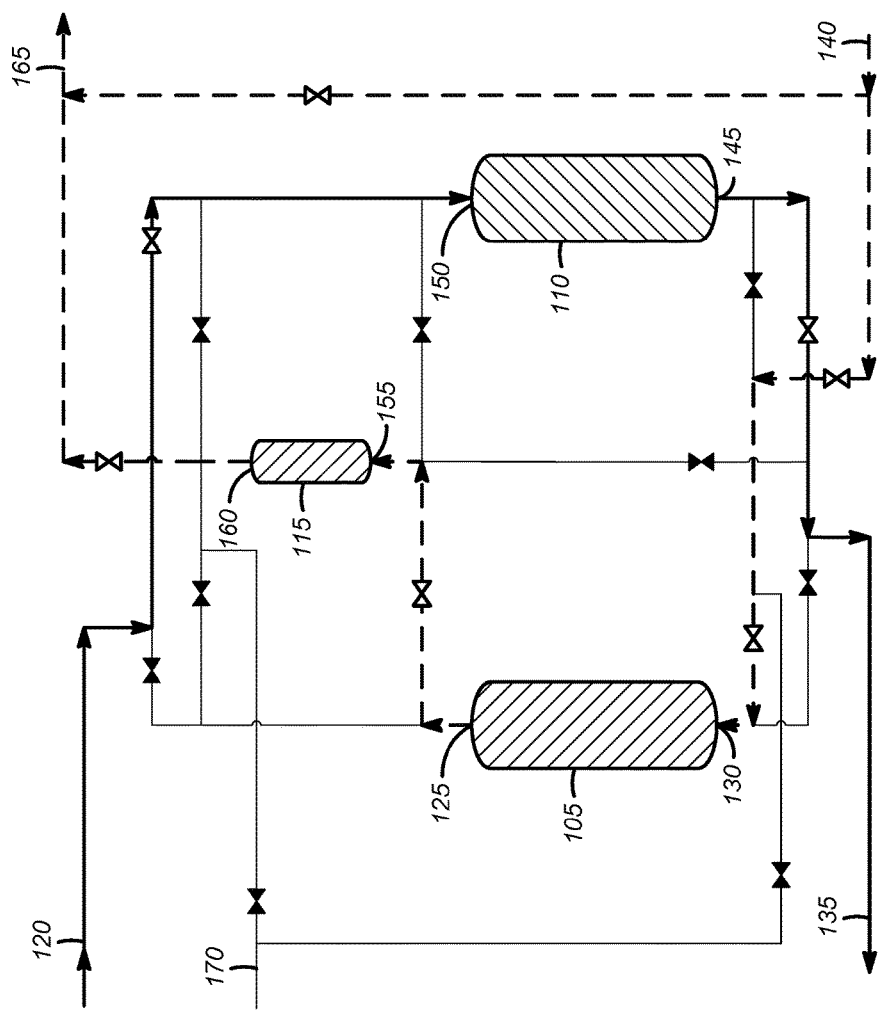

Fresh desorbent is then passed through the first adsorption bed 105 and the trim bed 115 to remove adsorbed material to regenerate them, as shown in FIG. 10. This forms additional spent desorbent, which passes out through the desorbent outlet 165. The untreated feed continues to pass through the second adsorption bed 110, and the additional treated feed continues to pass out through the product outlet 135. The first adsorption bed 110 is in downstream communication with the first desorbent inlet 140, the trim bed 115 is in downstream communication with the first adsorption bed 105, and the desorbent outlet 165 is in downstream communication with the trim bed 115. As illustrated the first desorbent inlet 140 is connected with the bottom 130 of the first adsorption bed 105, the top 125 of the first adsorption bed 105 is connected to the bottom 155 of the trim bed 115, and the top 160 of the trim bed 115 is connected with the desorbent outlet 165.

Figure 11:
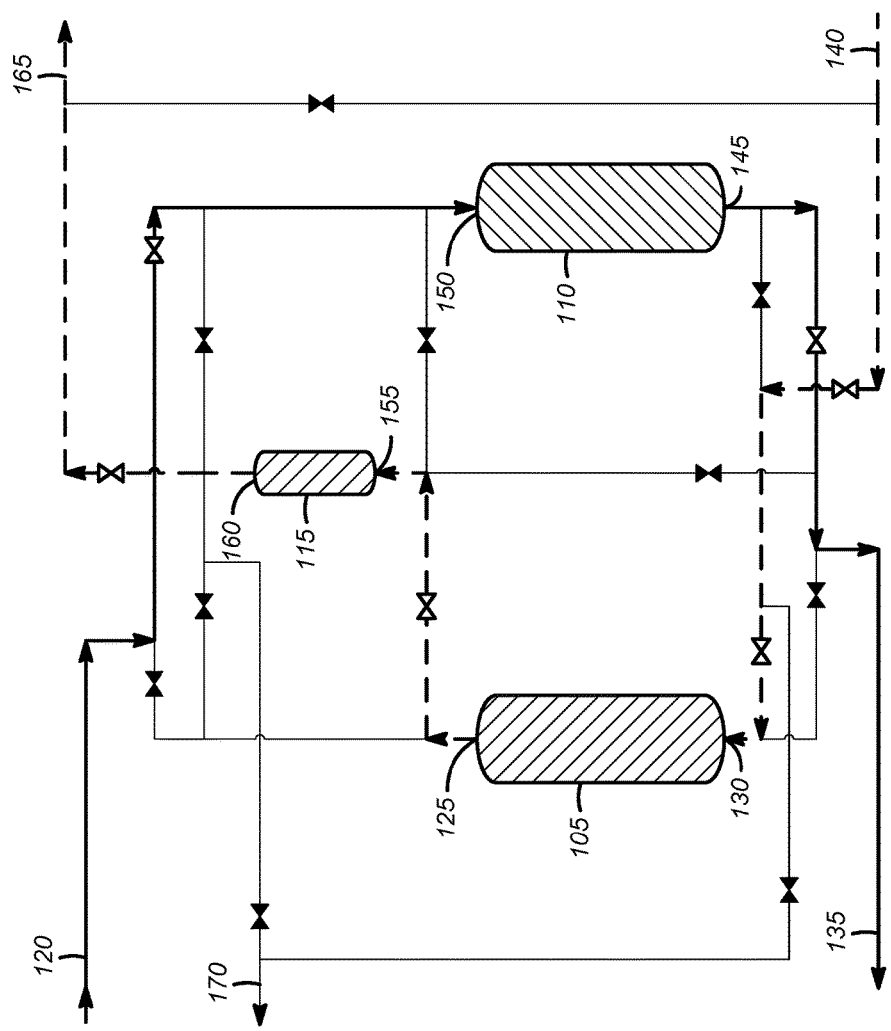

As shown in FIG. 11, the first desorbent inlet 140 is isolated from the desorbent outlet 165 while passing the fresh desorbent through the first adsorption bed 105 and the trim bed 115 to remove the adsorbed material to regenerate them. As illustrated, the desorbent outlet 165 is disconnected from the first desorbent inlet 140. It can be disconnected before beginning the regeneration or after regeneration has been started.

By about, we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a method for operating an adsorption separation zone comprising at least two adsorption beds and a trim bed in selective communication comprising passing an untreated feed through the first adsorption bed to produce treated feed, the treated feed passing out through a product outlet, while passing fresh desorbent through the second adsorption bed and the trim bed to remove adsorbed material from the second adsorption bed and the trim bed to regenerate the second adsorption bed and the trim bed forming spent desorbent, the spent desorbent passing out though a desorbent outlet; when the adsorbed material is desorbed from the second adsorption bed and the trim bed, stopping the flow of fresh desorbent to the second adsorption bed and the trim bed and isolating the second adsorption bed and the trim bed from the first desorbent inlet and the desorbent outlet, while continuing to pass the untreated feed through the first adsorption bed and continuing to pass the treated feed out through the product outlet; stopping the flow of the untreated feed to the first adsorption bed, and passing the untreated feed though the second adsorption bed to produce additional treated feed, the additional treated feed displacing the desorbent in the second adsorption bed, and the desorbent from the second adsorption bed passing to the first adsorption bed where the desorbent from the second adsorption bed displaces the treated feed in the first adsorption bed, the treated feed from the first adsorption bed passing to the trim bed where the treated feed displaces the desorbent in the trim bed, the desorbent from the trim bed and the treated feed from the first adsorption bed passing out through the product outlet; when substantially all of the desorbent is displaced from the second adsorption bed, isolating the first adsorption bed and the trim bed from the second adsorption bed and the product outlet, and passing the treated feed from the first adsorption bed and the trim bed to the second adsorption bed, while continuing to pass the untreated feed through the second adsorption bed and the additional treated feed out through the product outlet; passing a second desorbent through the first adsorption bed and the trim bed to remove any residual treated feed from the first adsorption bed, and continuing to pass the treated feed from the first adsorption bed and the trim bed to the second adsorption bed, while continuing to pass the untreated feed through the second adsorption bed and the additional treated feed out through the product outlet; when the residual treated feed is removed from the first adsorption bed, isolating the first adsorption bed from the second desorbent inlet, and passing the second desorbent through the trim bed to remove the treated feed from the trim bed and continuing to pass the treated feed from the first adsorption bed and the trim bed though the second adsorption bed, while continuing to pass the untreated feed through the second adsorption bed and the additional treated feed out through the product outlet; when the trim bed is full of the second desorbent, stopping the flow of the second desorbent, and isolating the trim bed from the second adsorption bed, while continuing to pass the untreated feed through the second adsorption bed and the additional treated feed out through the product outlet; passing the fresh desorbent through the first adsorption bed and the trim bed to remove adsorbed material from the first adsorption bed and the trim bed to regenerate the first adsorption bed and the trim bed forming additional spent desorbent, the additional spent desorbent passing out through the desorbent outlet, while continuing to pass the untreated feed through the second adsorption bed and the additional treated feed out through the product outlet. An embodiment of the invention is one, any or all of prior embodiments in this paragraph up through the first embodiment in this paragraph further comprising bypassing the fresh desorbent around the second adsorption bed and the trim bed after stopping the flow of the fresh desorbent to the second adsorption bed and the trim bed. An embodiment of the invention is one, any or all of prior embodiments in this paragraph up through the first embodiment in this paragraph further comprising isolating the first desorbent inlet from the desorbent outlet while passing the fresh desorbent through the first adsorption bed and the trim bed. An embodiment of the invention is one, any or all of prior embodiments in this paragraph up through the first embodiment in this paragraph wherein the untreated feed is passed through the first and second adsorption beds and the trim bed in a downflow arrangement, and the fresh desorbent is passed through the first and second adsorption beds and the trim bed in an upflow arrangement. An embodiment of the invention is one, any or all of prior embodiments in this paragraph up through the first embodiment in this paragraph wherein the untreated feed is passed through the first and second adsorption beds and the trim bed in a downflow arrangement, and the fresh desorbent is passed through the first and second adsorption beds and the trim bed in a downflow arrangement. An embodiment of the invention is one, any or all of prior embodiments in this paragraph up through the first embodiment in this paragraph wherein the untreated feed is passed through the first and second adsorption beds and the trim bed in an upflow arrangement, and the fresh desorbent is passed through the first and second adsorption beds and the trim bed in an upflow arrangement. An embodiment of the invention is one, any or all of prior embodiments in this paragraph up through the first embodiment in this paragraph wherein the first desorbent and the second desorbent are the same. An embodiment of the invention is one, any or all of prior embodiments in this paragraph up through the first embodiment in this paragraph further comprising separating the spent desorbent from the desorbent outlet in a separation zone into a recycle desorbent stream and a second stream. An embodiment of the invention is one, any or all of prior embodiments in this paragraph up through the first embodiment in this paragraph further comprising controlling a flow through the trim bed to maximize recovery of treated feed and minimize breakthrough of the adsorbed material. An embodiment of the invention is one, any or all of prior embodiments in this paragraph up through the first embodiment in this paragraph, wherein the untreated feed comprises mono-olefins, aromatics, and paraffins, the first and second desorbent are benzene, the treated feed comprises mono-olefins, and paraffins, and the first and second adsorption beds comprise a Na faujasite X zeolite adsorbent.

A second embodiment of the invention is a method for operating an adsorption separation zone comprising at least two adsorption beds and a trim bed in selective communication comprising passing an untreated feed through the first adsorption bed to produce treated feed, the treated feed passing out through a product outlet, while passing fresh desorbent through the second adsorption bed and the trim bed to remove adsorbed material from the second adsorption bed and the trim bed to regenerate the second adsorption bed and the trim bed forming spent desorbent, the spent desorbent passing out through a desorbent outlet, the first adsorption bed being in downstream communication with a feed inlet, and the product outlet being in downstream communication with the first adsorption bed, the second adsorption bed being in downstream communication with a first desorbent inlet, the trim bed being in downstream communication with the second adsorption bed, and the desorbent outlet being in downstream communication with the trim bed; when the adsorbed material is desorbed from the second adsorption bed and the trim bed, stopping the flow of fresh desorbent to the second adsorption bed and the trim bed, and isolating the second adsorption bed and the trim bed from the first desorbent inlet and the desorbent outlet, while continuing to pass the untreated feed through the first adsorption bed and continuing to pass the treated feed out through the product outlet; stopping the flow of the untreated feed to the first adsorption bed, and passing the untreated feed though the second adsorption bed to produce additional treated feed, the second adsorption bed being in downstream communication with the feed inlet, the first adsorption bed being in downstream communication with the second adsorption bed, the trim bed being in downstream communication with the first adsorption bed, and the product outlet being in downstream communication with the trim bed, the additional treated feed displacing the desorbent in the second adsorption bed, and the desorbent from the second adsorption bed passing to the first adsorption bed where the desorbent from the second adsorption bed displaces the treated feed in the first adsorption bed, the treated feed from the first adsorption bed passing to the trim bed where the treated feed from the first adsorption bed displaces the desorbent in the trim bed, the desorbent from the trim bed and the treated feed from the first adsorption bed passing out through the product outlet; when substantially all of the desorbent is displaced from the second adsorption bed, isolating the first adsorption bed and the trim bed from the second adsorption bed and the product outlet, and passing the treated feed from the first adsorption bed and the trim bed to the second adsorption bed, while continuing to pass the untreated feed through the second adsorption bed and the additional treated feed out through the product outlet, the second adsorption bed being in downstream communication with the feed inlet, and the product outlet being in downstream communication with the second adsorption bed; passing a second desorbent through the first adsorption bed and the trim bed to remove any residual treated feed from the first adsorption bed, and continuing to pass the treated feed from the first adsorption bed and the trim bed to the second adsorption bed, while continuing to pass the untreated feed through the second adsorption bed and the additional treated feed out through the product outlet, the first adsorption bed being in downstream communication with a second desorbent inlet, the trim bed being in downstream communication with the first adsorption bed, and the second adsorption bed being in downstream communication with the trim bed; when the residual treated feed is removed from the first adsorption bed, isolating the first adsorption bed from the second desorbent inlet, and passing the second desorbent through the trim bed to remove the treated feed from the trim bed and continuing to pass the treated feed from the first adsorption bed and the trim bed through the second adsorption bed, while continuing to pass the untreated feed through the second adsorption bed and the additional treated feed out through the product outlet, the trim bed being in downstream communication with the second desorbent inlet, the trim bed being in downstream communication with the first adsorption bed, and the second adsorption bed being in downstream communication with the trim bed; when the trim bed is full of the second desorbent, stopping the flow of the second desorbent, and isolating the trim bed from the second adsorption bed, while continuing to pass the untreated feed through the second adsorption bed and the additional treated feed out through the product outlet, the trim bed being in downstream communication with the first adsorption bed; passing the fresh desorbent through the first adsorption bed and the trim bed to remove adsorbed material from the first adsorption bed and the trim bed to regenerate the first adsorption bed and the trim bed forming additional spent desorbent, the additional spent desorbent passing out through the desorbent outlet, while continuing to pass the untreated feed through the second adsorption bed and the additional treated feed out through the product outlet, the first adsorption bed being in downstream communication with the first desorbent inlet, the trim bed being in downstream communication with the first adsorption bed, and the desorbent outlet being in downstream communication with the trim bed. An embodiment of the invention is one, any or all of prior embodiments in this paragraph up through the second embodiment in this paragraph further comprising bypassing the fresh desorbent around the second adsorption bed and the trim bed after stopping the flow of the fresh desorbent to the second adsorption bed and the trim bed, the desorbent outlet being in downstream communication with the first desorbent inlet. An embodiment of the invention is one, any or all of prior embodiments in this paragraph up through the second embodiment in this paragraph further comprising isolating the first desorbent inlet from the desorbent outlet while passing the fresh desorbent through the first adsorption bed and the trim bed. An embodiment of the invention is one, any or all of prior embodiments in this paragraph up through the second embodiment in this paragraph wherein the untreated feed is passed through the first and second adsorption beds and the trim bed in a downflow arrangement, and the fresh desorbent is passed through the first and second adsorption beds and the trim bed in an upflow arrangement. An embodiment of the invention is one, any or all of prior embodiments in this paragraph up through the second embodiment in this paragraph wherein the untreated feed is passed through the first and second adsorption beds and the trim bed in a downflow arrangement, and the fresh desorbent is passed through the first and second adsorption beds and the trim bed in a downflow arrangement. An embodiment of the invention is one, any or all of prior embodiments in this paragraph up through the second embodiment in this paragraph wherein the untreated feed is passed through the first and second adsorption beds and the trim bed in an upflow arrangement, and the fresh desorbent is passed through the first and second adsorption beds and the trim bed in an upflow arrangement. An embodiment of the invention is one, any or all of prior embodiments in this paragraph up through the second embodiment in this paragraph wherein the first desorbent and the second desorbent are the same. An embodiment of the invention is one, any or all of prior embodiments in this paragraph up through the second embodiment in this paragraph further comprising separating the spent desorbent from the desorbent outlet in a separation zone into a recycle desorbent stream and a second stream. An embodiment of the invention is one, any or all of prior embodiments in this paragraph up through the second embodiment in this paragraph further comprising controlling a flow through the trim bed to maximize recovery of treated feed and minimize breakthrough of the adsorbed material. An embodiment of the invention is one, any or all of prior embodiments in this paragraph up through the second embodiment in this paragraph, wherein the untreated feed comprises mono-olefins, aromatics, and paraffins, the first and second desorbent are benzene, the treated feed comprises mono-olefins, and paraffins, and the first and second adsorption beds comprise a Na faujasite X zeolite adsorbent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A method for operating an adsorption separation zone comprising at least two adsorption beds and a trim bed in selective communication comprising:
   passing an untreated feed through the first adsorption bed to produce treated feed, the treated feed passing out through a product outlet, while passing fresh desorbent through the second adsorption bed and the trim bed to remove adsorbed material from the second adsorption bed and the trim bed to regenerate the second adsorption bed and the trim bed forming spent desorbent, the spent desorbent passing out though a desorbent outlet;
   when the adsorbed material is desorbed from the second adsorption bed and the trim bed, stopping the flow of fresh desorbent to the second adsorption bed and the trim bed and isolating the second adsorption bed and the trim bed from the first desorbent inlet and the desorbent outlet, while continuing to pass the untreated feed through the first adsorption bed and continuing to pass the treated feed out through the product outlet;
   stopping the flow of the untreated feed to the first adsorption bed, and passing the untreated feed though the second adsorption bed to produce additional treated feed, the additional treated feed displacing the desorbent in the second adsorption bed, and the desorbent from the second adsorption bed passing to the first adsorption bed where the desorbent from the second adsorption bed displaces the treated feed in the first adsorption bed, the treated feed from the first adsorption bed passing to the trim bed where the treated feed displaces the desorbent in the trim bed, the desorbent from the trim bed and the treated feed from the first adsorption bed passing out through the product outlet;
   when substantially all of the desorbent is displaced from the second adsorption bed, isolating the first adsorption bed and the trim bed from the second adsorption bed and the product outlet, and passing the treated feed from the first adsorption bed and the trim bed to the second adsorption bed, while continuing to pass the untreated feed through the second adsorption bed and the additional treated feed out through the product outlet;
   passing a second desorbent through the first adsorption bed and the trim bed to remove any residual treated feed from the first adsorption bed, and continuing to pass the treated feed from the first adsorption bed and the trim bed to the second adsorption bed, while continuing to pass the untreated feed through the second adsorption bed and the additional treated feed out through the product outlet;
   when the residual treated feed is removed from the first adsorption bed, isolating the first adsorption bed from the second desorbent inlet, and passing the second desorbent through the trim bed to remove the treated feed from the trim bed and continuing to pass the treated feed from the first adsorption bed and the trim bed though the second adsorption bed, while continuing to pass the untreated feed through the second adsorption bed and the additional treated feed out through the product outlet;
   when the trim bed is full of the second desorbent, stopping the flow of the second desorbent, and isolating the trim bed from the second adsorption bed, while continuing to pass the untreated feed through the second adsorption bed and the additional treated feed out through the product outlet;
   passing the fresh desorbent through the first adsorption bed and the trim bed to remove adsorbed material from the first adsorption bed and the trim bed to regenerate the first adsorption bed and the trim bed forming additional spent desorbent, the additional spent desorbent passing out through the desorbent outlet, while continuing to pass the untreated feed through the second adsorption bed and the additional treated feed out through the product outlet.

2. The method of claim 1 further comprising:
   bypassing the fresh desorbent around the second adsorption bed and the trim bed after stopping the flow of the fresh desorbent to the second adsorption bed and the trim bed.

3. The method of claim 2 further comprising:
   isolating the first desorbent inlet from the desorbent outlet while passing the fresh desorbent through the first adsorption bed and the trim bed.

4. The method of claim 1 wherein the untreated feed is passed through the first and second adsorption beds and the trim bed in a downflow arrangement, and the fresh desorbent is passed through the first and second adsorption beds and the trim bed in an upflow arrangement.

5. The method of claim 1 wherein the untreated feed is passed through the first and second adsorption beds and the trim bed in a downflow arrangement, and the fresh desorbent is passed through the first and second adsorption beds and the trim bed in a downflow arrangement.

6. The method of claim 1 wherein the untreated feed is passed through the first and second adsorption beds and the trim bed in an upflow arrangement, and the fresh desorbent is passed through the first and second adsorption beds and the trim bed in an upflow arrangement.

7. The method of claim 1 wherein the first desorbent and the second desorbent are the same.

8. The method of claim 1 further comprising:
separating the spent desorbent from the desorbent outlet in a separation zone into a recycle desorbent stream and a second stream.

9. The method of claim 1 further comprising:
controlling a flow through the trim bed to maximize recovery of treated feed and minimize breakthrough of the adsorbed material.

10. The method of claim 1, wherein the untreated feed comprises mono-olefins, aromatics, and paraffins, the first and second desorbent are benzene, the treated feed comprises mono-olefins, and paraffins, and the first and second adsorption beds comprise a Na faujasite X zeolite adsorbent.

11. A method for operating an adsorption separation zone comprising at least two adsorption beds and a trim bed in selective communication comprising:
passing an untreated feed through the first adsorption bed to produce treated feed, the treated feed passing out through a product outlet, while passing fresh desorbent through the second adsorption bed and the trim bed to remove adsorbed material from the second adsorption bed and the trim bed to regenerate the second adsorption bed and the trim bed forming spent desorbent, the spent desorbent passing out through a desorbent outlet, the first adsorption bed being in downstream communication with a feed inlet, and the product outlet being in downstream communication with the first adsorption bed, the second adsorption bed being in downstream communication with a first desorbent inlet, the trim bed being in downstream communication with the second adsorption bed, and the desorbent outlet being in downstream communication with the trim bed;
when the adsorbed material is desorbed from the second adsorption bed and the trim bed, stopping the flow of fresh desorbent to the second adsorption bed and the trim bed, and isolating the second adsorption bed and the trim bed from the first desorbent inlet and the desorbent outlet, while continuing to pass the untreated feed through the first adsorption bed and continuing to pass the treated feed out through the product outlet;
stopping the flow of the untreated feed to the first adsorption bed, and passing the untreated feed though the second adsorption bed to produce additional treated feed, the second adsorption bed being in downstream communication with the feed inlet, the first adsorption bed being in downstream communication with the second adsorption bed, the trim bed being in downstream communication with the first adsorption bed, and the product outlet being in downstream communication with the trim bed, the additional treated feed displacing the desorbent in the second adsorption bed, and the desorbent from the second adsorption bed passing to the first adsorption bed where the desorbent from the second adsorption bed displaces the treated feed in the first adsorption bed, the treated feed from the first adsorption bed passing to the trim bed where the treated feed from the first adsorption bed displaces the desorbent in the trim bed, the desorbent from the trim bed and the treated feed from the first adsorption bed passing out through the product outlet;
when substantially all of the desorbent is displaced from the second adsorption bed, isolating the first adsorption bed and the trim bed from the second adsorption bed and the product outlet, and passing the treated feed from the first adsorption bed and the trim bed to the second adsorption bed, while continuing to pass the untreated feed through the second adsorption bed and the additional treated feed out through the product outlet, the second adsorption bed being in downstream communication with the feed inlet, and the product outlet being in downstream communication with the second adsorption bed;
passing a second desorbent through the first adsorption bed and the trim bed to remove any residual treated feed from the first adsorption bed, and continuing to pass the treated feed from the first adsorption bed and the trim bed to the second adsorption bed, while continuing to pass the untreated feed through the second adsorption bed and the additional treated feed out through the product outlet, the first adsorption bed being in downstream communication with a second desorbent inlet, the trim bed being in downstream communication with the first adsorption bed, and the second adsorption bed being in downstream communication with the trim bed;
when the residual treated feed is removed from the first adsorption bed, isolating the first adsorption bed from the second desorbent inlet, and passing the second desorbent through the trim bed to remove the treated feed from the trim bed and continuing to pass the treated feed from the first adsorption bed and the trim bed through the second adsorption bed, while continuing to pass the untreated feed through the second adsorption bed and the additional treated feed out through the product outlet, the trim bed being in downstream communication with the second desorbent inlet, the trim bed being in downstream communication with the first adsorption bed, and the second adsorption bed being in downstream communication with the trim bed;
when the trim bed is full of the second desorbent, stopping the flow of the second desorbent, and isolating the trim bed from the second adsorption bed, while continuing to pass the untreated feed through the second adsorption bed and the additional treated feed out through the product outlet, the trim bed being in downstream communication with the first adsorption bed;
passing the fresh desorbent through the first adsorption bed and the trim bed to remove adsorbed material from the first adsorption bed and the trim bed to regenerate the first adsorption bed and the trim bed forming additional spent desorbent, the additional spent desorbent passing out through the desorbent outlet, while continuing to pass the untreated feed through the second adsorption bed and the additional treated feed out through the product outlet, the first adsorption bed being in downstream communication with the first desorbent inlet, the trim bed being in downstream communication with the first adsorption bed, and the desorbent outlet being in downstream communication with the trim bed.

12. The method of claim 11 further comprising:
bypassing the fresh desorbent around the second adsorption bed and the trim bed after stopping the flow of the fresh desorbent to the second adsorption bed and the trim bed, the desorbent outlet being in downstream communication with the first desorbent inlet.

13. The method of claim 12 further comprising:
isolating the first desorbent inlet from the desorbent outlet while passing the fresh desorbent through the first adsorption bed and the trim bed.

14. The method of claim 11 wherein the untreated feed is passed through the first and second adsorption beds and the trim bed in a downflow arrangement, and the fresh desorbent is passed through the first and second adsorption beds and the trim bed in an upflow arrangement.

15. The method of claim 11 wherein the untreated feed is passed through the first and second adsorption beds and the trim bed in a downflow arrangement, and the fresh desorbent is passed through the first and second adsorption beds and the trim bed in a downflow arrangement.

16. The method of claim 11 wherein the untreated feed is passed through the first and second adsorption beds and the trim bed in an upflow arrangement, and the fresh desorbent is passed through the first and second adsorption beds and the trim bed in an upflow arrangement.

17. The method of claim 11 wherein the first and the second desorbent are the same.

18. The method of claim 11 further comprising:
separating the spent desorbent from the desorbent outlet in a separation zone into a recycle desorbent stream and a second stream.

19. The method of claim 11 further comprising:
controlling a flow through the trim bed to maximize recovery of treated feed and minimize breakthrough of the adsorbed material.

20. The method of claim 11, wherein the untreated feed comprises mono-olefins, aromatics, and paraffins, the first and second desorbent are benzene, the treated feed comprises mono-olefins, and paraffins, and the first and second adsorption beds comprise a Na faujasite X zeolite adsorbent.

* * * * *